United States Patent [19]
Arnold et al.

[11] Patent Number: 5,628,721
[45] Date of Patent: May 13, 1997

[54] BACK SUPPORT ASSEMBLY HAVING AN INFLATABLE AIR CUSHION

[75] Inventors: William K. Arnold, Pasadena, Calif.; Tracy E. Grim, Scottsdale, Ariz.

[73] Assignee: Royce Medical Company, Camarillo, Calif.

[21] Appl. No.: 624,300

[22] Filed: Mar. 29, 1996

[51] Int. Cl.$^6$ .................................................... A61F 5/00
[52] U.S. Cl. ........................ 602/19; 2/44; 128/118.1
[58] Field of Search ...................... 602/13, 19; 2/44; 450/155; 128/112.1, 117.1, 118.1

[56] References Cited

U.S. PATENT DOCUMENTS

| | | |
|---|---|---|
| Re. 34,883 | 3/1995 | Grim . |
| 3,441,027 | 4/1969 | Lehman . |
| 3,920,008 | 11/1975 | Lehman . |
| 4,135,503 | 1/1979 | Romano . |
| 4,178,923 | 12/1979 | Curlee . |
| 4,622,957 | 11/1986 | Curlee . |
| 4,682,588 | 7/1987 | Curlee . |
| 4,703,750 | 11/1987 | Sebastian et al. . |
| 4,756,306 | 7/1988 | Curlee . |
| 4,836,194 | 6/1989 | Sebastian et al. . |
| 4,993,409 | 2/1991 | Grim . |
| 5,062,414 | 11/1991 | Grim . |
| 5,111,806 | 5/1992 | Travis . |
| 5,195,948 | 3/1993 | Hill et al. . |
| 5,205,814 | 4/1993 | Lundrigan et al. . |
| 5,396,906 | 3/1995 | Harrold . |
| 5,399,150 | 3/1995 | Saunders . |
| 5,437,615 | 8/1995 | Pekar et al. ................ 602/19 |
| 5,450,858 | 9/1995 | Zablotsky et al. . |
| 5,470,000 | 11/1995 | Munoz . |
| 5,547,461 | 8/1996 | Levis ....................... 602/19 |

*Primary Examiner*—Linda C. Dvorak
*Attorney, Agent, or Firm*—Oppenheim Poms Smith

[57] ABSTRACT

A back support assembly including a bulb pump which when pumped or squeezed by the user inflates an air cushion to exert the desired pressure and fit against the user's lower back. The cushion is secured to the middle of the elastic belt, which is adapted to wrap around the user's back to position the air cushion against the middle of the user's back. Opposing adjustment straps are attached to the back of the strap. With the belt secured around the user the adjustment straps can be pulled and releasably secured to the belt and/or each other at respective positions exerting the desired force on the air cushion and against the user's back. The bulb pump is conveniently attached to and carried by one of the adjustment straps. It is secured to the rear of that strap, and has its rounded forward portion extending out through an opening in the strap, operatively accessible for inflation/deflation by the user. That is, with this mounting arrangement the bulb pump is out of the way, but still readily accessible for squeeze pumping action by the user, and by its shape, construction and location advantageously has a low profile.

20 Claims, 4 Drawing Sheets

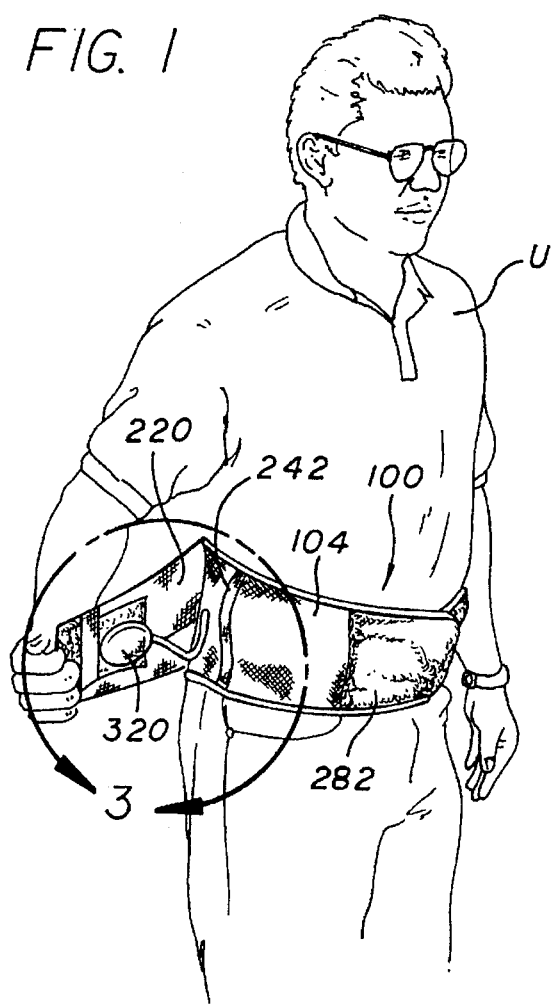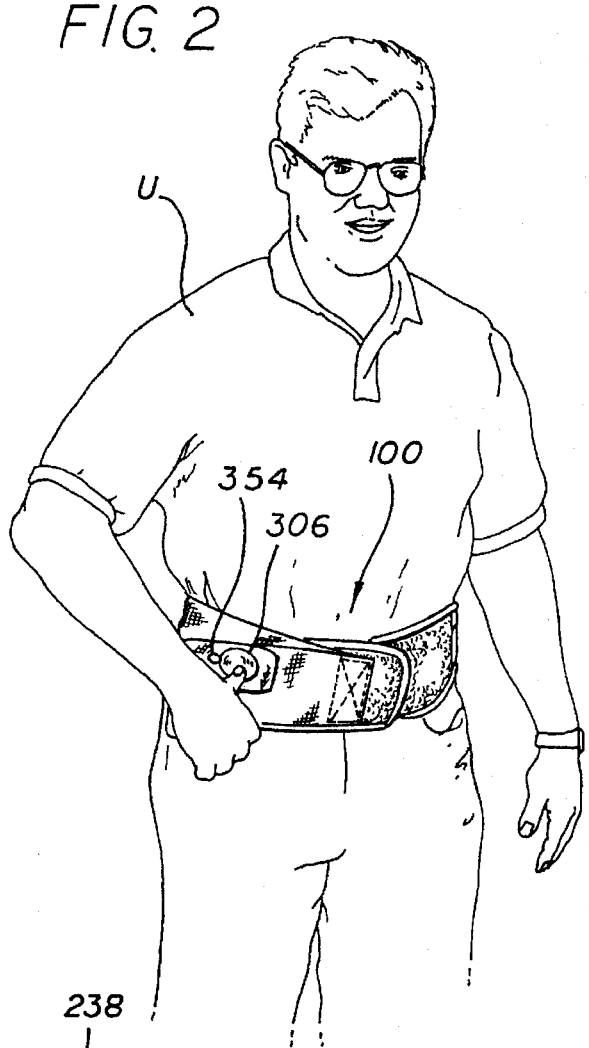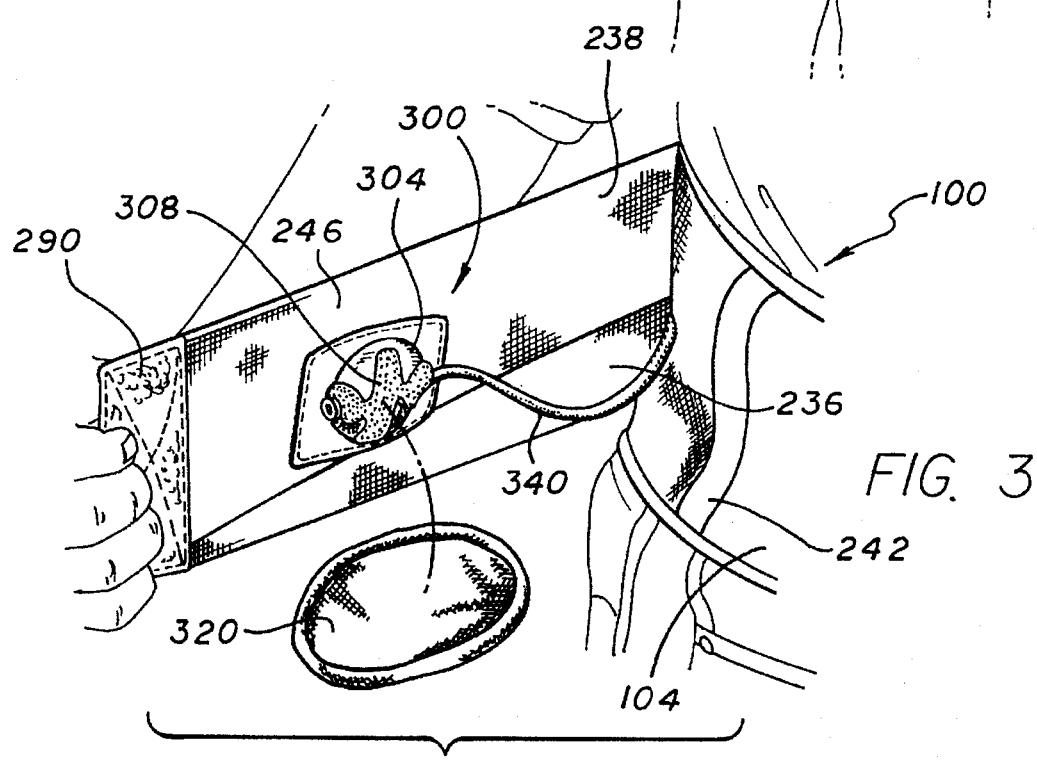

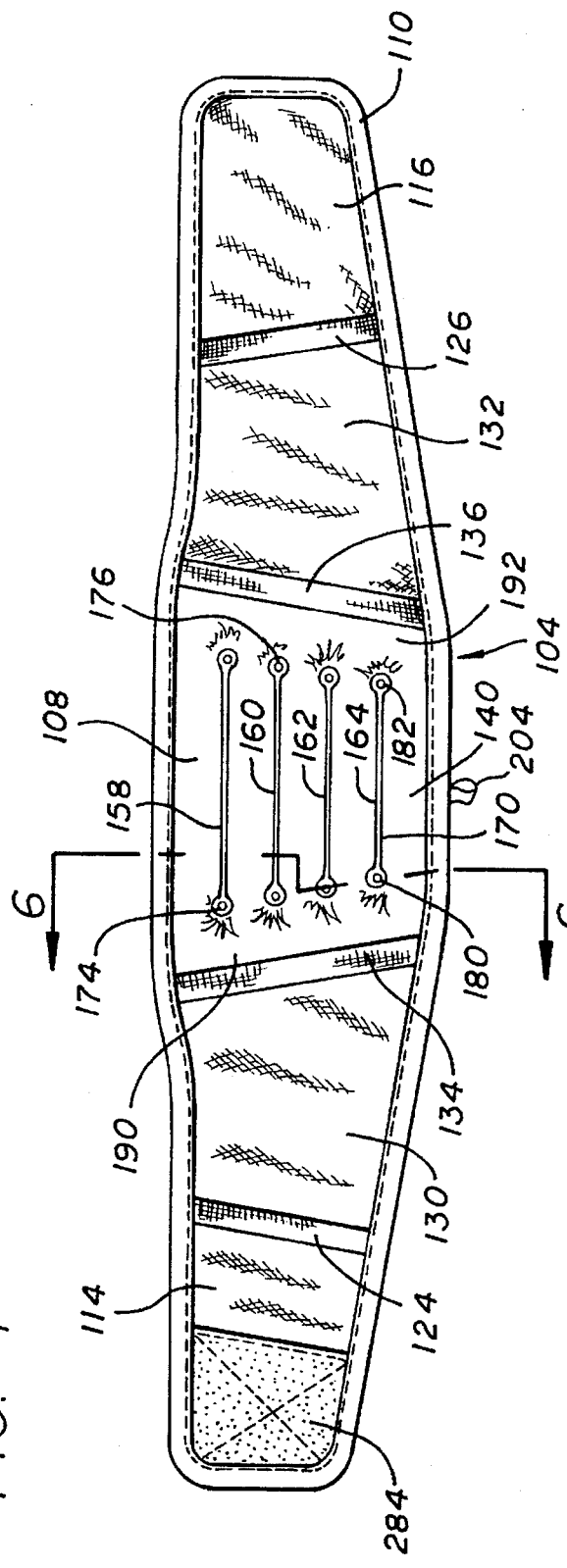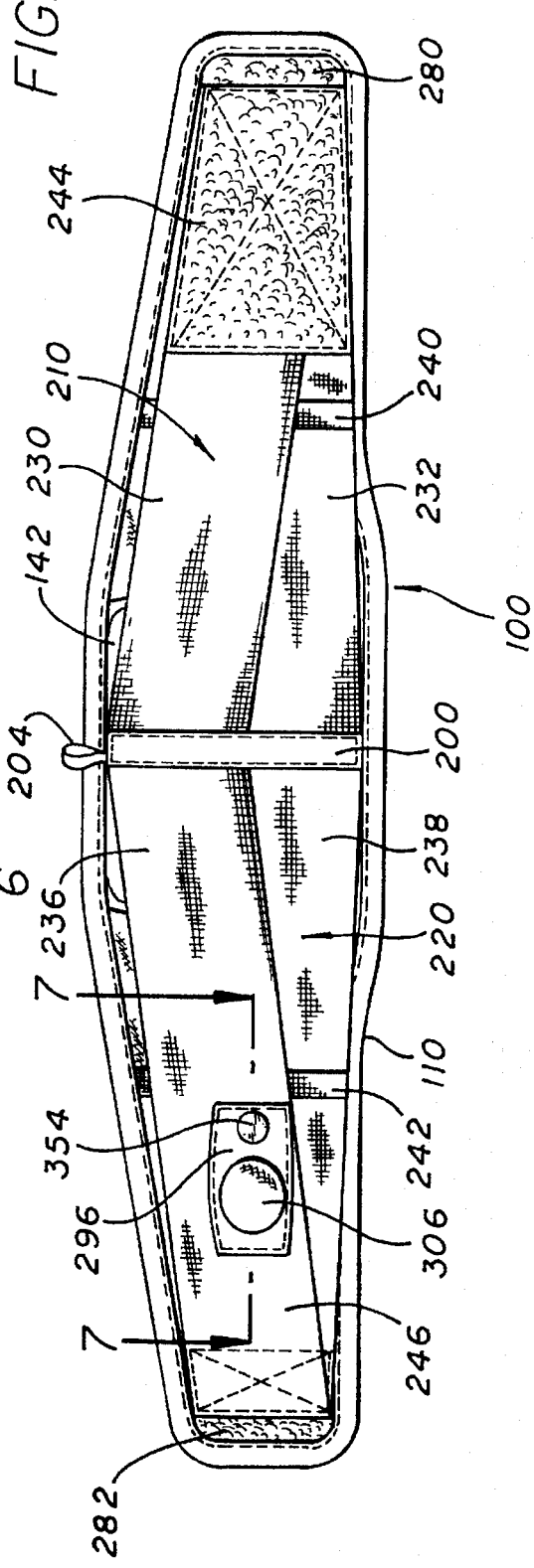
FIG. 4
FIG. 5

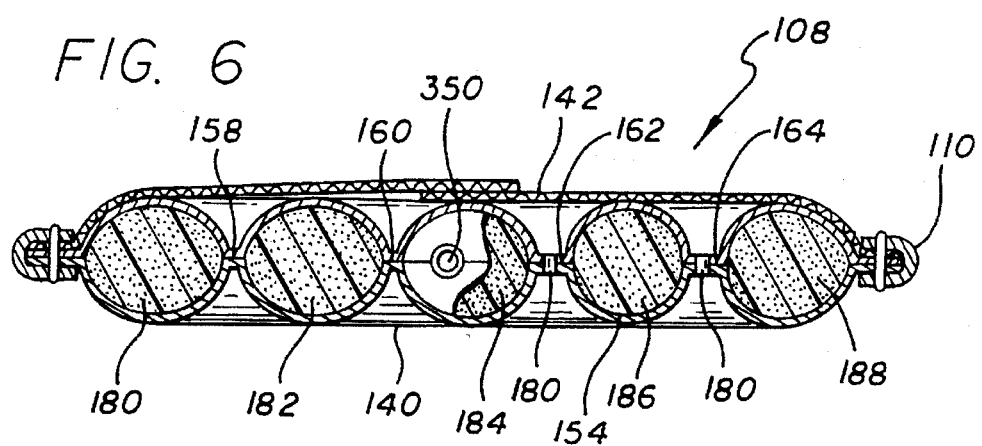
FIG. 6
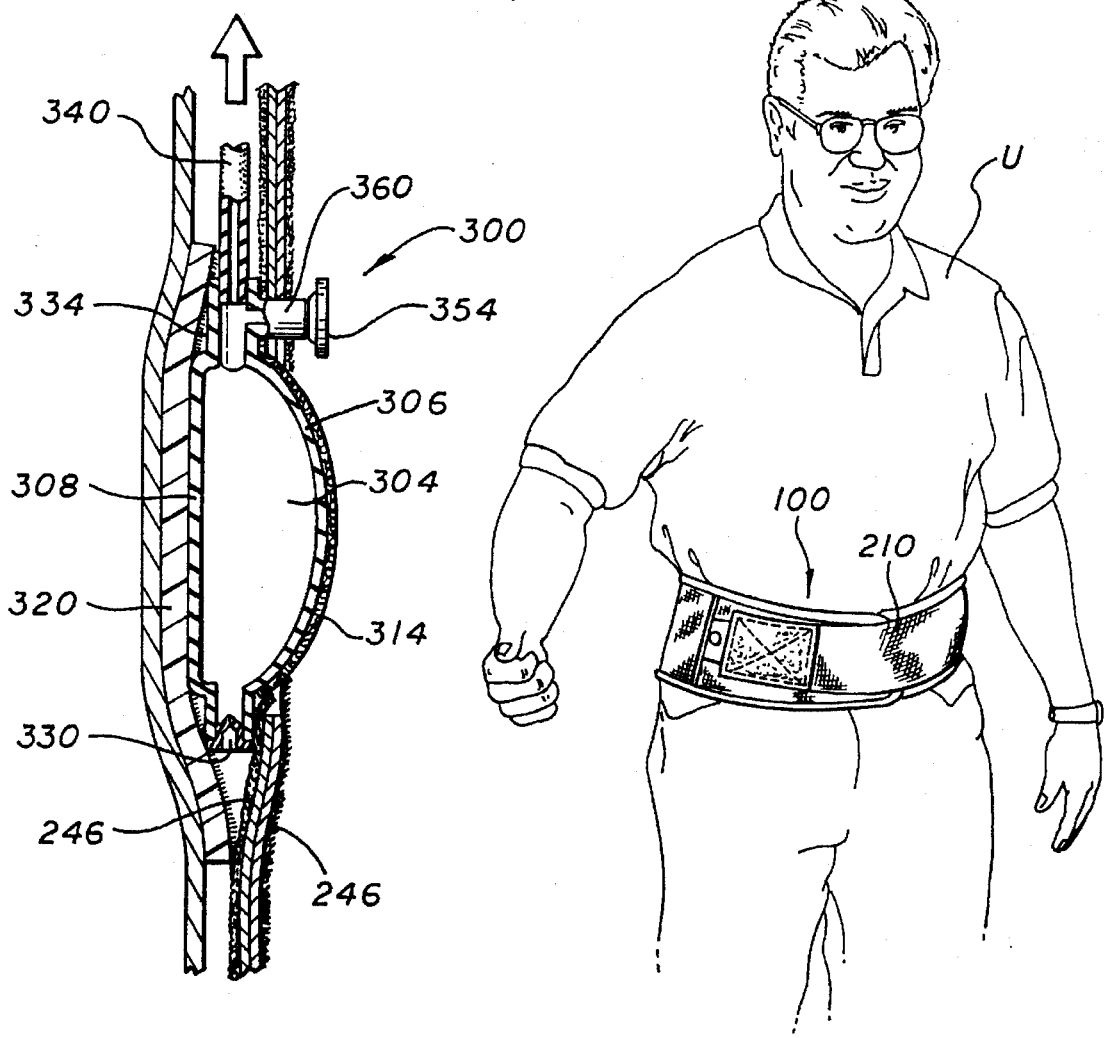
FIG. 7
FIG. 8

BACK SUPPORT ASSEMBLY HAVING AN INFLATABLE AIR CUSHION

BACKGROUND OF THE INVENTION

The present invention relates to a back support or brace having an air cushion for supporting and/or applying pressure against the sacrolumbar portion of a user's back. More specifically, it concerns such back supports having bulb pumps which can be squeezed by the user to adjust the inflation pressure in the air cushion.

Many people are affected with a variety of back problems relating to musculo-skeletal disorders. Proper treatment often requires the use of a back support device to aid in the recovery cycle and/or to administer various forms of therapy. Bracing by a support, application of hot and cold therapy, and limiting range of motion while assisting strength development are examples of the types of therapies frequently suggested to assist a weak or injured back. Back supports are also useful in preventing injury in the first place by adding support and encouraging proper form during strenuous and repetitive lifting activities. The variety of purposes and applications for back braces and the diverse body types of those who use them thus require a back support that is adjustable in support as well as versatile in the support it can provide. In other words, back supports can be used to apply localized pressure to specific areas of the lumbosacral or lower back to prevent and/or treat injuries.

One prior art back support is the "ProFlex" back support available from Ergodyne Corporation of St. Paul, Minn. It includes a breathable mesh belt having spaced lateral stays and ends with outward surface loop material. A first pair of pull straps is secured at one end to the outward center of the belt and overlaps and converges with a slight upward angle to opposite ends thereof. The opposite ends are secured together and have a piece of hook material attached to the inward surface and securable to the loop material at one of the ends. A second pair of pull straps extends in an opposite direction to define a flattened V-configuration with the first pair. The straps of the second pair have hook material at their inward joined ends which is securable to the opposite loop material of the belt.

Another prior art orthopaedic back support assembly is that disclosed in U.S. application Ser. No. 07/823,171, filed Jan. 21, 1992, commonly assigned herewith. That assembly includes a main body member which extends around the waist of a patient, and a V-configuration wide elastic strap which extends around the back of the patient with the center of the elastic strap extending down to a substantially lower level at the center of the patient's back than the ends of the strap at the sides of the patient. The back support assembly can also include a pressure applicator such as an air bladder and pad. The pressure applicator and the V-configuration strap can be mounted within, and can be secured to the main body member after passing through slots in the body member.

A further example of a prior art back brace is the Industrial Back Brace as disclosed in copending U.S. application Ser. No. 08/234,012, filed Apr. 28, 1994. Briefly, it has an elastic belt assembly with a central belt portion, overlapping belt straps extending out from both ends of that portion to form opposing belt ends and overlapping pull straps extending out from the center back portion to the belt ends. A lumbo-sacral pad is affixed to the inward face of the portion. When the belt assembly is wrapped around the user's waist and the belt ends releasably secured to one another with the desired fit, the belt straps and the pull straps pull the pad against the "small" of the user's back. The pad has spaced buttons or fusion welds and can be a pre-inflated air cushion or a (soft or hard) foam cushion. Spaced lateral stays sewn into the central portion give the belt rigidity as well as flexibility to conform to the user's back. In lieu of or in addition to the stays, a flexible plastic sheet internal to the bladder can be used. The belt straps and the central portion are made of lightweight breathable material. Holes punched through each of the fusion welds promote air circulation through to the user's adjacent back. A hot/cold gel pad can be releasably secured with hook-and-loop fasteners to the inward surface of the pad for applying hot or cold therapy to the user's back. Examples of other "pull" type straps for belts are shown in U.S. Pat. Nos. 3,441,027 (Lehman), 3,920,008 (Lehman), 5,111,806 (Travis), 5,399,150 (Saunders), and 5,470,000 (Munoz). (These patents and all other patents, publications or applications mentioned anywhere in this disclosure are hereby incorporated by reference in their entireties.)

The prior art cushions can include cushioning material and/or an air cushion. And the air cushion can have a fixed non-adjustable air volume or pressure, or can be pressure or volume adjustable. This adjustment can be by a user-operable bulb pump. Examples of pumps are shown in U.S. Pat. Nos. 4,135,503 (Ramano), 4,622,957 (Curlee), 4,682,588 (Curlee), 4,703,750 (Sebastian, et at.), 4,756,306 (Curlee), 4,836,194 (Sebastian, et at.), 4,993,409 (Grim), 5,195,448 (Hill, et al.), 5,205,814 (Lundrigan), 4,396,906 (Harold) and Re. 34,883 (Grim). However, the prior art pump arrangements can be bulky, dangling down from the side of the belt, not easily accessible to the user, and/or easily misplaced.

SUMMARY OF THE INVENTION

Directed to remedying the problems in the prior art, disclosed herein is a back support assembly having an elastic belt adapted to wrap around the user's waist and its ends releasably secured together. An air cushion is secured to the center of the belt for positioning against the user's lower back. A pair of V-shaped pull straps are attached to the outside center of the belt and extend in opposite directions towards but not all of the way to respective ends of the belt. By pulling on these V-straps and releasably attaching them in place with hook/loop fasteners the force and fit of the air cushion against the user's back as desired by the user are provided. Also, squeezing or pressing a bulb pump operatively connected to the air cushion allows the user to adjust the inflation pressure of the air cushion as desired for comfort and/or therapy.

The bulb pump is carried by one of the pull straps, and is secured out of the way to a bottom surface of the strap. Its rounded top surface protrudes out through a hole in the strap so as to be readily visible and accessible to the user. An on-off dial or valve operatively connected to the pump through an opening in the strap is positioned on the outside surface of the same pull strap. Flexible tubing disposed between the belt and the pull strap provides fluid pressure communication between the bulb pump and the air cushion.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 1 is a perspective view of an inflatable back support assembly of the present invention shown being positioned on a user;

FIG. 2 is a view similar to FIG. 1 showing the user activating the bulb pump of the assembly;

FIG. 3 is an enlarged view taken on circle 3 of FIG. 1 and showing the protector panel removed;

FIG. 4 is a rear elevational view of the assembly of FIG. 1 shown flat;

FIG. 5 is a front (upside down) elevational view thereof;

FIG. 6 is an enlarged cross-sectional view taken on line 6—6 of FIG. 4;

FIG. 7 is an enlarged cross-sectional view taken on line 7—7 of FIG. 5;

FIG. 8 is a view similar to FIGS. 1 and 2 showing the assembly in an alternative adjustment pull strap position; however, the preferred alternative position is the opposite to that shown; that is, the right pull strap on top of the left;

DETAILED DESCRIPTION OF PREFERRED EMBODIMENTS OF THE INVENTION

Figure 9:
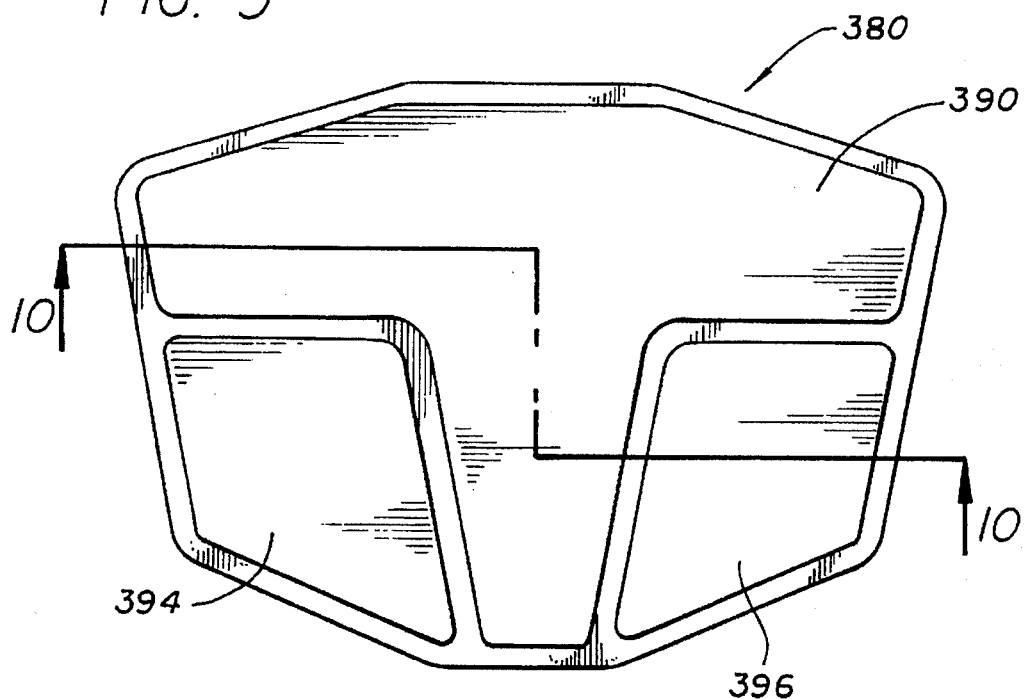
FIG. 9 is a front (inward) elevational view of a gel pad of the present invention.

Referring to the drawings, an inflatable back support assembly of the present invention is illustrated generally at 100. Many of the surfaces of different components are defined herein as being "inward" or "outward"; these directions are relative to a user U who is wearing the assembly 100. The assembly 100 includes a stretchable back support belt shown generally at 104 and an inflatable pad or cushion shown generally at 108 and secured at a central (inward) location to the belt.

The belt 104 is formed of a number of pieces of elastic material sized and secured together by sewing or otherwise. A reinforcing rim 110 of strong elastic material is folded over the perimeter of the belt 104 and sewn in place. Referring to FIG. 4, the belt 104 includes end pieces 114, 116 of a loop (Velcro) foam trico laminate material. On one end a panel 120 of hook-type (Velcro) material is sewn. Angled reinforcing strips 124, 126 of rubber gripper tape material connect inner edges of the end pieces 114, 116 to respective breathable mesh panels 130, 132 of mesh Lycra-Nylon. Additional strips 134, 136 of rubber gripper tape material connect inner edges of the mesh panels 130, 132 with outer edges of the cushion 108. These strips 134, 136 each define a pocket holding an elongated (plastic) stay therein.

Referring to FIG. 6, the cushion 108 is formed of two sheets 140, 142, both of which have inside (relative to the cushion) surfaces comprising thin films or coatings of urethane plastic material. The inward sheet 140 is a urethane/plastic-nylon laminate material, and the outward sheet 142 is also a urethane/plastic-nylon laminate material. A layer of open-cell urethane foam 154 having a thickness of ¾ inch and a density of 2.0 pounds is disposed between the sheets 140, 142 and has four elongate horizontal cutouts as can be understood from FIG. 6. Thereby the two sheets 140, 142 (or more specifically their inside films) can be fused directly together in a radio frequency welding procedure, or otherwise sealed together. The foam 154 is not sandwiched between the fused sheets 140, 142 at the fusion points, since the sheets are fused in the cutout areas of the foam.

These fusion welds 158, 160, 162, 164 are preferably shaped as elongate "dumb bell shapes," as can be understood from FIG. 4, with narrow elongate portions 170 and enlarged heads 174, 176 at both ends thereof. Ventilation holes 180, 182 (each about 1/16 inch in diameter) are punched through centers of each of the heads 174, 176. The holes 180, 182 thereby pass entirely through the cushion 108 and promote the circulation of cooling and drying ventilation air on the user's back. Instead of the elongate dumb bell shapes of the welds, other shapes can be used, such as small dot welds with a hole punched in the center of each.

The welds 158, 160, 162, 164 help define horizontal chambers 180, 182, 184, 186, 188 in the cushion 108 communicating with end chambers 190, 192 (FIG. 4). The air in these chambers and more particularly within the open-cell foam 154 can flow between the chambers to conform to different users and uses and to apply pressure at the desired areas on the user's back. The volume of air within the cushion 108 can be adjusted as needed by the user and as will be discussed in detail later in this disclosure. Also, the foam 154 can be contoured for specific orthopedic uses and can at least partially fill in the gaps in the lumbar curve of the user's back and thereby improve support and comfort of the back brace assembly 100.

The welds 158, 160, 162, 164 prevent the cushion 108 from balling up or bulging against the user's back. The air can then move within the cushion 108 to occupy previously untilled areas in the cushion to increase the pressure rate on the muscles of the small of the user's back. That is, the welds 158, 160, 162, 164 can limit the height or thickness of the cushion 108 and provide the amount of air needed in various areas of the cushion to better support the user's back.

Referring to FIG. 5, a vertical sleeve 200 extends from the top to the bottom of the belt 104 and is sewn at its ends to the perimeter rim 110 at the back of the belt. A plastic stay or rib is held in the sleeve 200 and extends substantially the entire length or height thereof. Velcro hook-type material on the inward face of the sleeve 200 releasably attaches to the outward loop-type surface of the cushion's outward sheet 142 to releasably hold the sleeve against the back or outward surface of the belt 104. A loop 204 at the bottom of the sleeve 200 functions as a centering or bottom location indicator.

Left and right pull strap assemblies shown generally at 210 and 220 are sewn at their inward edges to the sleeve 200. They extend outward from the sleeve 200 in opposite directions and at slightly oblique angles. Each pull strap assembly 210, 220 includes two strap members 230, 232 and 236, 238, overlapping in an outwardly converging V-shape, and loosely held relative to the belt 104 by vertical belt straps 240, 242. The outward ends of the strap members of each pair 230, 232 and 236, 238 are secured together as by sewing at respective securement areas 244, 246. Each of the strap members 230, 232, 236, 238 is formed of a stretchable elastic material (combination of polyester yarn and rubber filaments).

The belt 104 has at both ends thereof on outward surfaces, loop-type (Velcro) material 280, 282. Thereby with the belt 104 around the user's waist the ends can be pulled towards one another in an overlapping arrangement to the desired tightness around the waist. The hook material 284 is then mated to the opposite loop-type material at the desired location.

With the belt wrapped around the waist and secured, the securement area 242, 244 of the pull strap assemblies 210, 220 are then pulled around the user's waist and the hook-type Velcro pads 290 on interior surfaces at the desired tension locations and mated to either the outward pads 280, 282 on the belt or on the other loop-type material 244. When the pull strap assemblies 210, 220 are pulled or cinched tight, the cushion 108 is pulled against the user's back with the desired force and orientation. Strap 220 can overlap onto strap 210 for additional support, in a reverse arrangement to that shown in FIG. 8.

The stays in sleeves 134, 136, 200 are made of rigid or semi-rigid plastic. They give the cushion 108 and central portion of the belt 104 transverse rigidity or form. They are not inflexible, however. When the pull strap assemblies 210, 220 are pulled and secured in place with the desired force, they will tend to bend, flex or curve with the small of the user's back, following its contours to provide additional support to the user's back. That is, they go from a linear to a curved configuration to tailor up to the curvature of the user's back.

The amount or volume of air in the cushion 108 and thereby the pressure and shape of the cushion can be adjusted by actuation of a bulb pump assembly as shown generally at 300 in FIGS. 1, 2, 3, 5 and 7. The bulb pump assembly 300 includes a bulb pump 304 having a rounded front surface 306 and a flattened rear surface 308. Bulb pump 304 can have a height dimension of 1.3, a width dimension of 2.0, a length dimension of 2.2, and an effective pumping volume of 16.8 cubic inches. A round opening is cut or otherwise formed in a central portion of the securement area of one of pull strap assemblies 220 and through an inward hook-type panel 246, as illustrated in FIGS. 3 and 7. A cover 314 of loop-type material is glued, taped or otherwise secured to the bulb pump 304. By placing the rounded front surface 306 out through the opening, the loop-type cover 314 and hook-type material 246 contact each other and securely mate together. This holds the bulb pump 304 in position in the opening and to the inward surface of the securement area of the pull strap assembly 220.

A flap or panel 320 having an outward surface of loop-type material is placed over the flattened rear side 308 of the bulb pump 302. The perimeter of the panel 320 is mated with the hook-type panel 246 securely holding the panel in place protectively covering and hiding the bulb pump 308. However, the panel 320 does not close the inlet end 330 of the bulb pump 308 through which air passes into the bulb pump by the suction or vacuum force when the bulb pump is compressed and released.

When the bulb pump 308 is compressed, air passes out the rigid short tubular end 334 thereof into the flexible tubing 340, as shown in FIGS. 1, 3 and 7. The opposite end of the flexible tubing 340 is fitted onto an inlet nipple of the cushion 108. The nipple then communicates through an inlet 350, as best shown in FIG. 6, with the interior of the cushion 108. Thus, when the bulb pump 308 is compressed or squeezed, by the user as depicted in FIG. 2 for example, air drawn in through the inlet end 330 is pumped though the flexible tubing 340 into the cushion 108 through inlet 350, as shown in FIG. 6. Additional compressions of the bulb pump 308 inflate the cushion 108 to the desired pressure.

Then when it is desired to reduce the pressure in the cushion 108, the dial 354 as shown in FIGS. 2, 5, 7 and 8 is turned from a closed position to an open position and air pressure released. As can be understood from FIG. 7, the dial 354 forms an enlarged head on the outward end of a rigid tube 360. The tube 360 passes through an opening in the securement area and through the hook panel 246 and fits on a T-shaped tube 366 on the outlet tube on the inward side of the securement area. Other valve constructions aside from the depicted dial valve 354 can be used as would be apparent to those skilled in the art. The loop-type material panel 296 surrounds the rounded bulb 306 and the dial valve 354, as can be seen in FIG. 5.

The bulb pump assembly 300 thereby is held in place on, carried by and incorporated into the pull strap assembly 220. It does not dangle such that it can be damaged, become lost, get caught or be uncomfortable to the user. Instead, it is built into the pull strap assembly 220 with an attractive low profile. Only a small rounded surface 306 thereof is exposed for easy and convenient access. The release valve 354 similarly has a secure, low profile and convenient mounting. All of the flexible tubing 340 connecting the bulb pump 308 to the cushion 108 is hidden out of view, concealed and not exposed to damage behind the pull strap assembly 220. More specifically, with the back support assembly 100 in place on the user, the flexible tubing 340 is safely and directly sandwiched between the inward surface of the pull strap assembly 220 and the outward surface of the belt 104. In addition to being inflation and fit adjustable, the back support assembly is also stretchable, lightweight and comfortable, and because of the mesh materials used and its ventilation holes, it is breathable.

Figure 10:
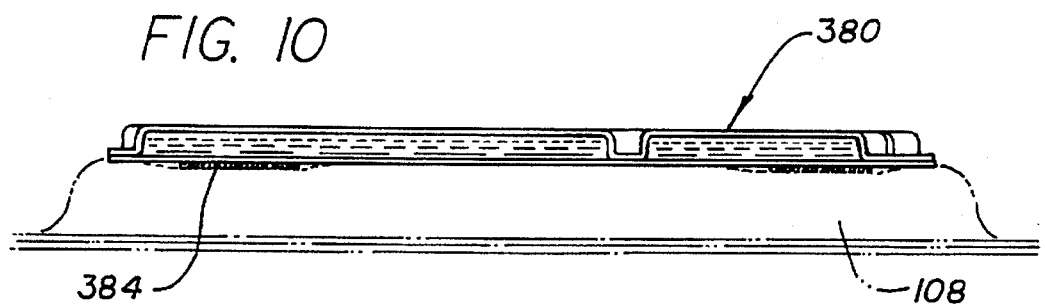
FIG. 10 is a cross-sectional view taken on line 10—10 of FIG. 9 and showing the gel pad attached to the air cushion of the assembly of FIG. 1.
Figure 11:
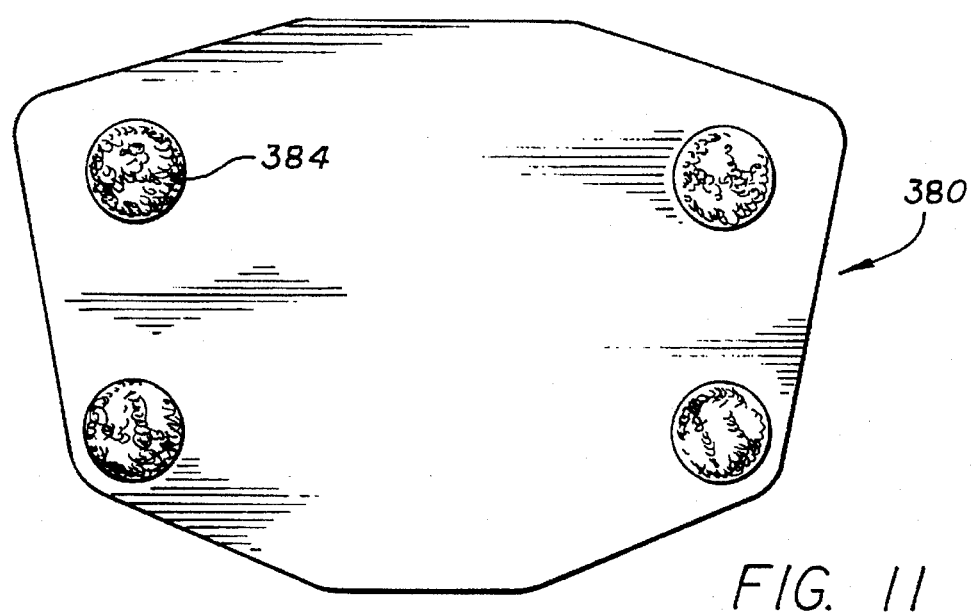
FIG. 11 is a rear (outward) elevational view of the gel pad.

As shown in FIGS. 9 through 11 generally at 380, a gel pad can be provided constructed of material known in the art. Examples of gel pads are the "Eclipse" gel pad available from Royce Medical Company of Camarillo, Calif., and those described in U.S. Pat. Nos. 4,671,267 (Stout) and 5,027,801 (Grim). On the outward surface of the gel pad 380 are patches 384 of hook-type material. These patches 384 are adapted to engage to the inward loop-type surface 140 of the cushion 108 to releasably hold the pad 380 to the cushion. This attachment is shown in FIG. 11. As best shown in FIGS. 10 and 11, gel pad 380 includes a T-shaped gel chamber 390 and two lower side chambers 394, 396. This configuration of the chambers advantageously conforms to the user's back in an orthopedically correct manner. The gel pad 380 is used for applying hot and/or cold therapeutic and/or comfort treatments to the user as would be apparent to those skilled in the art from this disclosure.

From the foregoing detailed description, it will be evident that there are a number of changes, adaptations and modifications of the present invention which come within the province of those skilled in the art. However, it is intended that all such variations not departing from the spirit of the invention be considered as within the scope thereof as limited solely by the claims appended hereto.

What is claimed is:

1. An inflatable back support assembly, comprising:
   a back support belt having belt ends releasably securable together when wrapped around a user's waist;
   an air cushion attached to said back support belt;
   first and second opposing adjustment pull straps attached to said back support belt;
   a manually-operable bulb pump mounted to and carried by said first strap; and
   tubing providing fluid communication between said bulb pump and said air cushion such that when said bulb pump is manually pumped, with said back support belt in place around the user, the inflation of said air cushion is adjusted.

2. The assembly of claim 1 wherein said bulb pump is mounted to an interior surface of said first strap and is accessible through an exterior surface of said first strap.

3. The assembly of claim 2 wherein said bulb pump has a generally flat rear surface.

4. The assembly of claim 1 wherein said first strap has a through-hole and said bulb pump is operatively accessible through said through-hole.

5. The assembly of claim 4 wherein said bulb pump protrudes a distance out said through-hole.

6. The assembly of claim 4 wherein said bulb pump is secured to an interior surface of said first strap, and said bulb pump has a rounded front surface extending out said through-hole and a generally flat rear surface between said first strap and said belt and facing said belt.

7. The assembly of claim 1 further comprising a panel attached to a rear surface of said first strap and covering said bulb pump.

8. The assembly of claim 7 wherein said panel is releasably secured with hook/loop material about its perimeter to said rear surface.

9. The assembly of claim 1 further comprising a fluid flow dial operatively connected to said bulb pump and operatively accessible at an exterior surface of said first strap.

10. The assembly of claim 9 wherein said dial extends out an opening in said first strap.

11. The assembly of claim 1 wherein said tubing comprises flexible tubing disposed between said first strap and said back support belt.

12. The assembly of claim 1 wherein said first strap includes two strap members secured to said back support belt in an outwardly converging V-shape and outward ends thereof secured together in an outer end securement area.

13. The assembly of claim 12 wherein said bulb pump is secured to a rear side of said securement area.

14. The assembly of claim 12 wherein said securement area has a throughhole and a rounded front portion of said bulb pump extends out through said through-hole beyond a front side of said securement area.

15. The assembly of claim 14 further comprising hook/loop releasable securing material on said front side and generally around said rounded front portion.

16. The assembly of claim 12 further comprising hook/loop releasable securing material on a rear side of said securement area and hook/loop releasable securement material on a front side of said securement area.

17. The assembly of claim 1 further comprising hook/loop material on said belt ends adapted to releasably mate with one another to secure said belt around the user's waist.

18. The assembly of claim 1 wherein said bulb pump is secured to a rear side of said first strap, has a rounded front portion extending out through an opening in said first strap, and has a flattened rear side adjacent to said back support belt.

19. The assembly of claim 18 further comprising a flow control member on a front side of said first strap and operatively connected to said bulb pump through an opening in said first strap.

20. The assembly of claim 1 further comprising a gel pad attachable to an interior surface of said air cushion to apply hot/cold therapy to the user's back with said back support belt wrapped around the user's waist.

* * * * *